Jan. 30, 1962 E. S. BOERNER Plant Pat. 2,129
ROSE PLANT
Filed March 17, 1961
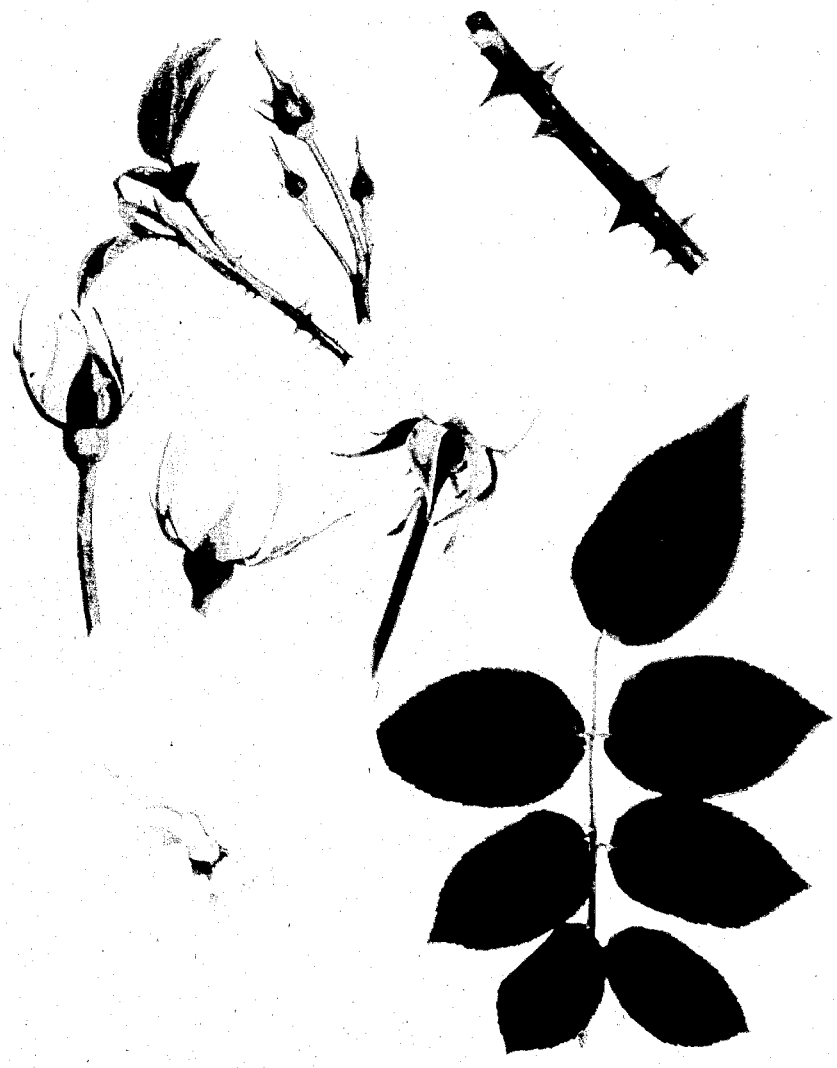
Inventor.
E. S. Boerner
By: Robb & Robb
Attorneys.

United States Patent Office

Plant Pat. 2,129
Patented Jan. 30, 1962

2,129
ROSE PLANT

Eugene S. Boerner, Newark, N.Y., assignor to Jackson & Perkins Company, Newark, N.Y., a corporation of New York Filed Mar. 17, 1961, Ser. No. 96,631
1 Claim. (Cl. 47—61)

The present invention relates to a new and distinct variety of rose plant of the floribunda class, which was originated by me by crossing an unnamed and unpatented red-flowered seedling of "Chatter" (Plant Patent No. 739) with the variety known as "Garnette Supreme" (Plant Patent No. 1,318).

The primary objective of this breeding was to produce a new rose variety which bears red flowers that have the long-keeping qualities of the parent variety "Garnette Supreme," but of larger flower size, combined with greater flower production. This objective was fully achieved, as evidenced by the following unique combination of characteristics which are outstanding in the new variety and which distinguish it from its parents, as well as from all other varieties of which I am aware:

(1) Prolific flower production throughout the entire growing season;

(2) Excellent cutting value as greenhouse bench plants;

(3) Long-lasting flower qualities; and (4) A distinctive Brilliant Scarlet Red general color tonality of the flowers, lightly overcast with Spectrum Red, which is unusual and different from any other rose of this type.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed red-flowered seedling of "Chatter."
- *Pollen parent.*—"Garnette Supreme."

Classification:
- *Botanic.*—Floribunda.
- *Commercial.*—Floribunda.

*Flower*

(Observations made from specimens grown in a greenhouse at Newark, New York, in the early morning during the latter part of the month of August.)

Blooming habit: Recurrent—continuous, with prolific production throughout the growing season.

Bud:
- *Size.*—Medium.
- *Form.*—Ovoid; is not affected by wet or hot weather.
- *Color.*—When sepals first divide—Carmine, Plate 1. When petals being to unfurl—Carmine, Plate 1, lightly overcast with Scarlet Red, Plate 1. When half-blown: inside of petals—Scarlet Red, Plate 1, lightly overcast with Carmine, Plate 1; reverse of petals—Scarlet Red, Plate 1.
- *Sepals.*—Branched; curl back when petals begin to unfurl. Color: inside—Absinthe Green, Plate 31; outside—Yellowish Oil Green, Plate 5.

- *Calyx.*—Color—Lettuce Green, Plate 5. Shape—pear. Size—small. Aspect—smooth. Odor when rubbed—none.
- *Peduncle.*—Length — medium. Aspect — smooth. Strength—erect; slender. Color—Lettuce Green, Plate 5.
- *Opening.*—Opens up well; is not affected by adverse weather conditions.

Bloom:
- *Size.*—Medium. Average size when fully expanded—3½ inches.
- *Borne.*—Both singly and several together.
- *Stems.*—Medium length; strong.
- *Form (when first open).*—Cupped. Permanence—retains its form to the end, but outer petals curl back.
- *Petalage.*—Double (full but open center). Number of petals under normal conditions—from 35 to 40.
- *Color.*—Center of flower—Scarlet Red, Plate 1. Outer petals—Spectrum Red, Plate 1. Base of petals (aiglet)—Sea-Foam Yellow, Plate 31. Inside of petals—Scarlet Red, Plate 1, lightly overcast with Spectrum Red, Plate 1. Reverse of petals—Pomegranate Purple, Plate 12, lightly overcast with Rose Red, Plate 12. General tonality from a distance—Scarlet Red, Plate 1, lightly overcast with Spectrum Red, Plate 1.
- *Discoloration.*—General tonality at end of first day—Scarlet Red, Plate 1. Second day—Scarlet Red, Plate 1, lightly overcast with Spectrum Red, Plate 1. Third day—Spectrum Red, Plate 1.

Petals:
- *Texture.*—Leathery; is not affected by wet or hot weather.
- *Appearance.*—Inside—satiny. Outside—shiny.
- *Form.*—Oval.
- *Arrangement.* — Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—very long. As cut flower—very long.

*Genital organs*

Stamens, anthers: Medium size; many; regularly arranged around styles. Color—Buff Yellow, Plate 4.

Stamens, filaments (threads): Medium length. Color—Sea-Foam Yellow, Plate 31.

Pollen: Color—Maize Yellow, Plate 4.

Styles: Columnar; uneven length; short; thin.

Stigmas: Color—Cream Color, Plate 16.

Ovaries: All enclosed in calyx.

Hips: None.

Seeds: None.

*Plant*

Form: Bush.

Growth: Very vigorous; upright.

Foliage: Compound of 5–7 leaflets.
- *Size.*—Large.
- *Quantity.*—Abundant.
- *Color.*—New foliage: upper side—Van Dyke Red, Plate 13, lightly overcast with Brick Red, Plate 13; under side —Acajou Red, Plate 13. Old foliage: upper side—Forest Green, Plate 17; under side—Light Bice Green, Plate 17, with edges lightly overcast with Van Dyke Red, Plate 13.
- *Shape.*—Oval.
- *Texture.* — Upper side — leathery. Under side—smooth.

*Ribs and veins.*—Ordinary.

*Edge.*—Serrated (saw-toothed).

*Serration.*—Both double and single; small.

*Leaf stem.*—Color—Absinthe Green, Plate 31. Under side—prickly.

*Stipules.*—Medium length; serrated.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: on main stalks from base—many; on laterals from stalk—many. Form—narrow base; medium length; hooked downward. Color (when young)—Lime Green, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of prolific flower production throughout the growing season, excellent cutting value as greenhouse bench plants, long lasting flower qualities, and a distinctive and unusual general color tonality of the flowers corresponding to Brilliant Scarlet Red, lightly overcast with Spectrum Red.

No references cited.

UNITED STATES PATENT OFFICE

Certificate of Correction

Plant Pat. No. 2,129 January 30, 1962

Eugene S. Boerner

It is hereby certified that error appears in the above numbered patent requiring correction.

The present sheet of drawing should be cancelled and the attached sheet substituted therefor, as part of the Letters Patent.

Signed and sealed this 15th day of May 1962.

[SEAL]

Attest:
ERNEST W. SWIDER,
*Attesting Officer.*

DAVID L. LADD,
*Commissioner of Patents.*

Jan. 30, 1962 E. S. BOERNER Plant Pat. 2,129
ROSE PLANT
Filed March 17, 1961
2 of 2
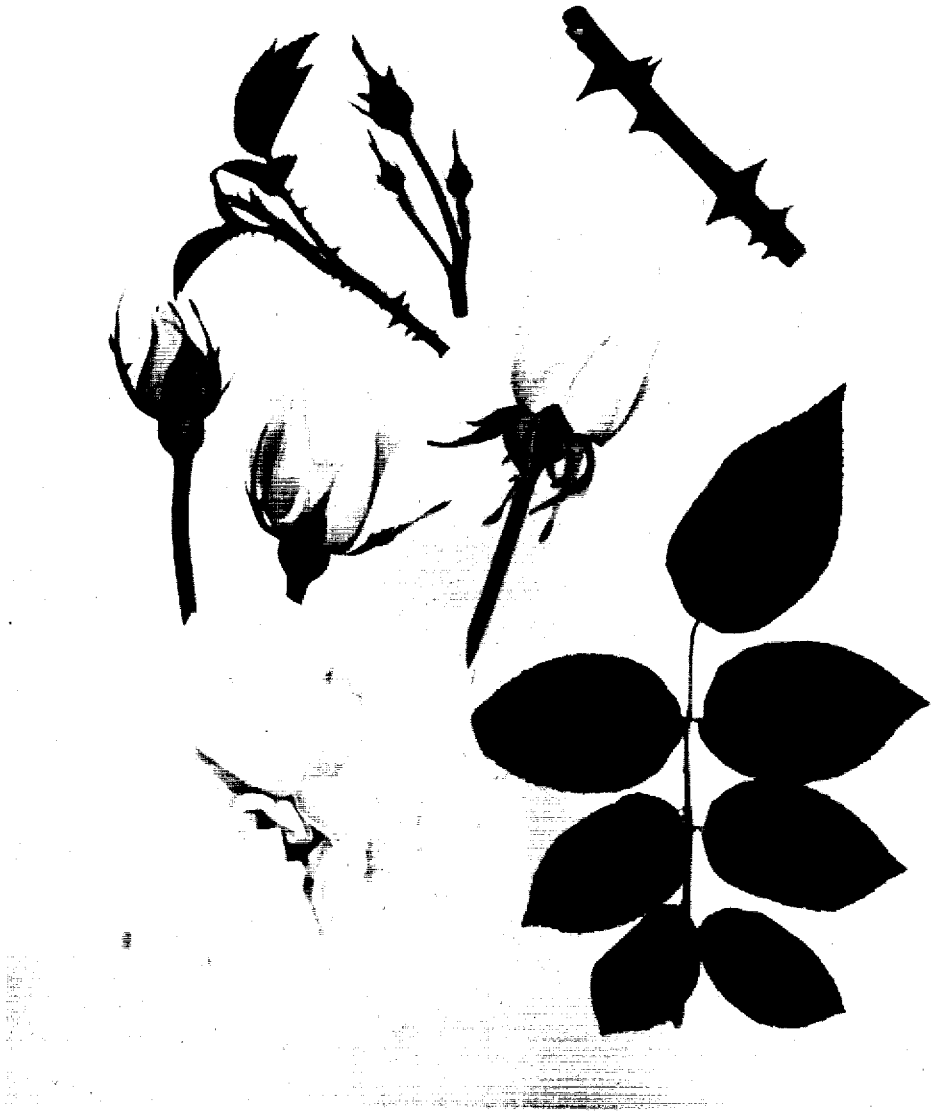
Inventor.
E. S. Boerner
By: Robb & Robb
Attorneys.